US010660573B2

(12) United States Patent
Ranganathan et al.

(10) Patent No.: US 10,660,573 B2
(45) Date of Patent: May 26, 2020

(54) SENSOR GUIDE WIRE WITH SHAPE MEMORY TIP

(71) Applicant: ST. JUDE MEDICAL COORDINATION CENTER BVBA, Zaventem (BE)

(72) Inventors: Sathees Ranganathan, Sundbyberg (SE); Anna Norlin-Weissenrieder, Lidingö (SE); Rolf Hill, Järfälla (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 1449 days.

(21) Appl. No.: 14/206,720

(22) Filed: Mar. 12, 2014

(65) Prior Publication Data

US 2014/0276224 A1    Sep. 18, 2014

Related U.S. Application Data

(60) Provisional application No. 61/779,618, filed on Mar. 13, 2013.

(51) Int. Cl.
*A61B 5/00*   (2006.01)
*A61M 25/09*  (2006.01)

(52) U.S. Cl.
CPC .  *A61B 5/6851* (2013.01); *A61M 2025/09141* (2013.01)

(58) Field of Classification Search
CPC ...... A61B 2017/00867; A61B 18/1492; A61B 2017/00243
See application file for complete search history.

(56) References Cited

U.S. PATENT DOCUMENTS 4,310,354 A * 1/1982 Fountain ............... B22F 1/0003
                                                    419/31
6,156,046 A  12/2000 Passafaro et al.
(Continued)

FOREIGN PATENT DOCUMENTS

EP    0 823 261 B1    5/2003
EP    1 849 409 A1   10/2007
(Continued)

OTHER PUBLICATIONS

International Search Report and Written Opinion dated Aug. 21, 2014, 13 pgs.
Japanese Office Action and English translation, dated Jul. 26, 2016, 13 pages.

*Primary Examiner* — Patrick Fernandes
(74) *Attorney, Agent, or Firm* — Foley & Lardner LLP (57) ABSTRACT

A sensor guide wire for intravascular measurements of at least one physiological or other variable in a living body, comprising a proximal region, a distal sensor region, and a tip region, and at least one sensor element arranged in said sensor region and configured to measure the variable and to generate a sensor signal in response to the variable. The sensor guide wire further comprises a core wire, with a tip core wire portion, wherein at least part of the tip core wire portion comprises a shape memory material, and the composition of the shape memory material is such that the transformation temperature of the shape memory material is above the body temperature of the living body.

15 Claims, 3 Drawing Sheets

(56) References Cited

U.S. PATENT DOCUMENTS

| | | | |
|---|---|---|---|
| 6,167,763 B1 * | 1/2001 | Tenerz | A61B 5/0215 73/756 |
| 6,248,083 B1 | 6/2001 | Smith et al. | |
| 6,575,920 B2 | 6/2003 | Zhou | |
| RE39,863 E | 10/2007 | Smith | |
| 7,670,302 B2 * | 3/2010 | Griffin | A61L 31/022 600/585 |
| 8,728,010 B2 | 5/2014 | Hirshman | |
| 2003/0120181 A1 * | 6/2003 | Toma | A61L 31/022 600/585 |
| 2004/0167436 A1 | 8/2004 | Reynolds et al. | |
| 2005/0273020 A1 | 12/2005 | Whittaker et al. | |
| 2006/0064055 A1 * | 3/2006 | Pile-Spellman | A61M 25/0105 604/95.05 |
| 2008/0077049 A1 | 3/2008 | Hirshman | |
| 2009/0227902 A1 * | 9/2009 | Simpson | A61M 25/09 600/585 |
| 2010/0159117 A1 * | 6/2010 | Griffin | A61L 31/022 427/2.11 |
| 2011/0054351 A1 * | 3/2011 | Fox | A61M 25/09 600/585 |

FOREIGN PATENT DOCUMENTS

| | | | | |
|---|---|---|---|---|
| JP | 2007-296354 A | 11/2007 | | |
| JP | 2010-501273 A | 1/2010 | | |
| WO | WO 2009/054800 A1 | 4/2009 | | |
| WO | WO 2011120565 A1 * | 10/2011 | | A61B 5/0215 |
| WO | WO 2012/041905 A1 | 4/2012 | | |

* cited by examiner

SENSOR GUIDE WIRE WITH SHAPE MEMORY TIP

BACKGROUND

The present invention relates to a sensor guide wire, and in particular to a sensor guide wire provided with a tip region.

Today, there is an increased need for invasive measurements of physiological variables. For example, when investigating cardiovascular diseases, it is strongly desired to obtain local measurements of blood pressure, flow and temperature in order to evaluate the condition of the subject under measurement. Therefore, methods and devices have been developed for disposing a miniature sensor inside the body of an individual at a location where the measurements should be performed, and for communicating with the miniature sensor in order to provide the physician or medical technician with critical information as to the status of a patient's condition. Typically, the miniature sensor is arranged at a distal end of a guide wire, which is generally known in the art, and used for example in connection with treatment of coronary disease.

The distal end of the guide wire is inserted into the body of a patient, for example into an opening into the femoral artery, and placed at a desired location. Once the guide wire is placed by the physician into the appropriate location, the miniature sensor can measure e.g. the blood pressure, temperature, position and/or flow. Measurement of blood pressure is a way to diagnose e.g. the significance of a stenosis. For evident reasons, the dimensions of the sensor and the guide wire are fairly small; the guide wire typically has a diameter of 0.35 mm. The sensor element may for example be embodied by an elongated, essentially rectangular chip with a pressure sensitive member in the form of a membrane provided thereon.

In order to power the sensor and to communicate signals representing the measured physiological variable to a control unit acting as an interface device disposed outside the body, one or more microcables for transmitting the signals are connected to the sensor, and are routed along the guide wire to be passed out from the vessel to an external control unit via a connector assembly. Most commonly extremely thin electrical cables are provided inside the guide wire, which itself is provided in the form of a tube (having an outer diameter of e.g. 0.35 mm), oftentimes made of stainless steel. In order to increase the bending strength and maneuverability of the tubular guide wire, a core wire is positioned inside the tube. The mentioned electrical leads are positioned in the space between the inner lumen wall and the core wire. Furthermore, the sensor chip is often arranged in a short tube, also referred to as a jacket or a sleeve. The jacket is hollow and accommodates, besides the sensor chip, also a portion of a core wire and often at least one microcable. A first coil may be attached to the distal end of the jacket, usually enclosing a distal tip portion of the core wire. Optionally a second coil may be attached to the proximal end of the jacket. The first and second coils may be attached to the respective end of the jacket, e.g. by gluing, welding or alternatively soldering. One purpose of the first coil is to enable steering the sensor guide wire through winding blood vessels. To help the user easily guide the wire through such tortuous vessel systems, the distal coil is often radiopaque, such that it is visible on an angiogram.

A large flexibility of the sensor guide wire is advantageous in that it allows the sensor guide to be introduced into small and tortuous vessels. It should, however, also be recognized that if the core wire is too flexible, it would be difficult to push the sensor guide forward into the vessels, i.e. the sensor guide wire must possess a certain "pushability" and a certain "torquability". Additionally, the sensor guide must be able to withstand the mechanical stress exerted on the core wire especially in sharp vessel bends.

Several different designs of sensor guide wires are known in the prior art, and examples of such sensor guide wires are disclosed in U.S. Pat. No. 6,167,763 B1, which describes the cantilevered mounting of the sensor element, U.S. RE39863 E, which discloses the sensor element and U.S. Pat. No. 6,248,083 B1, showing the complete sensor guide wire assembly, which all are assigned to the same assignee as in the present application, and which are hereby all incorporated by reference for the medical devices, components, materials, techniques, and methods described therein.

A further example of a sensor guide wire is disclosed in WO 2009/054800 A1, assigned to the present assignee, which is incorporated by reference herein in its entirety for the medical devices, components, materials, techniques, and methods described therein. The sensor guide wire has a proximal shaft region, a flexible region and a distal sensor region, and a tip region. The tip region of the sensor guide wire is provided with a tip core wire at least partly enclosed by a distal coil.

To improve navigation through tortuous vessels or to ease crossing a lesion in the vessel, the user, typically a physician performing a procedure, will oftentimes manually shape the tip of the wire at a slight angle before inserting the sensor guide wire into the patient. During the progression of the insertion through the vessels, the physician will often remove the wire and reshape the tip several times by hand. The reshaping is done in two steps; 1) straightening of the wire tip back to its original shape and 2) reshaping of the wire to a desired curve. Repeating these steps increases the risk of inducing permanent deformation in the wire, leading to reduced mechanical performance and risk of breakage. Furthermore, it is time consuming for the user.

SUMMARY

According to one embodiment, a sensor guide wire for intravascular measurement of at least one physiological or other variable in a living body includes a proximal region, a distal sensor region, and a tip region. The sensor guide wire further includes at least one sensor element arranged in the sensor region, and comprising a sensor portion, configured to measure the variable and generate a sensor signal in response to the variable, and a core wire, comprising a tip core wire portion extending at least partially along the tip region of the sensor guide wire and having a length. At least part of the tip core wire portion comprises a shape memory material having a transformation temperature, and the composition of the shape memory material is such that the transformation temperature of the shape memory material is above the body temperature of the living body.

According to another embodiment, a method of shaping and reshaping a tip region of a sensor guide wire for intravascular measurement of at least one physiological or other variable in a living body includes shaping the tip region manually by hand or with a suitable tool, wherein the tip region has an initial shape prior to the shaping, and wherein the tip region includes a tip core wire portion comprising at least partly a shape memory material, the shape memory material having a transformation temperature above body temperature of the living body; and heating the tip region to above said transformation temperature, causing the tip region to revert to the initial shape.

DETAILED DESCRIPTION

Although stainless steel is the most common material for a core wire in a guide wire, other materials are also used, such as nitinol. Nitinol is the common name for nickel-titanium alloys. Nitinol and other shape memory alloys exhibit two unique properties, super-elasticity and shape memory. These two properties are distinct from each other, and are defined by the transformation temperature of the alloy.

Shape memory alloys exhibit two crystal forms, austenite and martensite. Austenite is the stronger, high temperature form, and martensite is the softer, low temperature form. The transformation between the two is defined by the transformation temperature of the specific alloy, such that by simply heating or cooling, the alloy will go through a phase transformation from one form to the other.

In the martensite form, the shape memory alloy is easily deformed. When the alloy is then heated above the transformation temperature it instantly reverts to its austenite form and recovers its shape with great force. This is called the shape memory effect and is fully repeatable.

The transformation temperature is actually a short range of degrees, and can be fine-tuned by different parameters, such as altering the composition of the alloy, and using different processing techniques during manufacture. The processing techniques include using varying amounts of cold working and deformation, heat treatment and, more recently, also laser processing. However, the most common method for achieving a specific transformation temperature is to alter the ratio of metals in the alloy. For instance, by changing the ratio of nickel to titanium in nitinol, the transformation temperature can be changed from above +100 degrees C. to below −100 degrees C.

The critical points in the transformation are, during cooling, the martensite start temperature ($M_s$) and martensite finish temperature ($M_f$), and during heating, the austenite start temperature ($A_s$) and austenite finish temperature ($A_f$). A typical difference between start and finish temperature is 15-20 degrees Celsius. Also, the temperature range for transformation during cooling, i.e. the range $M_s$-$M_f$ is usually about 20-30 degrees Celsius lower than the temperature range for transformation during heating, i.e. the $A_s$-$A_f$ range.

Shape memory alloys also exhibit a superelastic behavior if deformed at a temperature slightly above the transformation temperature. This is due to the fact that local stress on the austenite form will transform the alloy locally to martensite, as long as the stress is maintained. Notably, when the stress is removed, the alloy reverts back to austenite.

A commercially available form of nitinol alloys are so called "linear elastic" nitinol, which is closely related to superelastic nitinol. By using cold work, directional stress and heat treatment, this type of alloy is manufactured such that it does not display a substantial "superelastic plateau" in the stress/strain curve. Instead, there is an essentially linear relation between stress and recoverable strain until plastic deformation begins. In some embodiments, a linear elastic nitinol does not exhibit any martensite and austenite phase changes.

Nitinol is used in core wires for guide wires primarily because of its superelastic or linear elastic properties. These properties give the wire a springy, rubberlike quality during bending while maintaining a strong core wire in the non-bent regions. Therefore, guide wires made of nitinol use alloys with transformation temperatures well below body temperature, even as low as 0 degrees C. Using nitinol instead of stainless steel eliminates the risk of kinking the wire, and provides a guide wire that can better follow the tortuous path in e.g. a blood vessel, and still rotate smoothly. However, such nitinol guide wires are not shapeable by the user. One example of such a guide wire is shown in US 2004/0167436.

Attempts have been made to use the shape memory effect in guide wires. One such example is in U.S. Pat. No. 7,670,302 which discloses a guide wire comprising a super-elastic nitinol core wire and a shape memory polymer tip in the form of a jacket covering the distal tip of the core wire. The tip is shapeable, but the procedure to do so is time consuming and complicated, as it involves constraining the tip in a desired shape, thereafter going through a series of heat setting steps before being released.

EP 823 261 discloses a guide wire comprising a distal coil and distal tip of the core wire made of nitinol. The core wire tip can slide within the tip, such that in the retracted position, the core wire tip takes the shape of an outer tube, and in the extended position, the core wire tip reverts to a preformed shape that was given to it prior to its insertion into the outer tube.

U.S. Pat. No. 6,575,920 shows a distal tip portion for a guide wire, which comprises two tip members that are coupled together. The first member is a core wire and the second member a sheath arranged proximally of the tip, wherein the sheath can comprise superelastic nitinol.

Nitinol can also be used as an actuator to help steer a guide wire through tortuous vessels. In US 2005/0273020, a guide wire is described comprising a variable tip made of shape memory alloy which deflects when remotely actuated by an electrical current, whereby the nitinol is heated to initiate a shape change. When the electrical current is switched off, the nitinol will cool and resume its initial shape.

The inventors of the present invention have identified a need for a sensor guide wire tip with improved reshaping ability and improved resistance to permanent deformation and fatigue.

An object of the present invention is to achieve a sensor guide wire in which the tip is easier to reshape by the user than in prior art sensor guide wires.

A further object of the present invention is to provide a sensor guide wire with improved navigation, facilitating maneuvering through the various bends and turns in the vessels.

Still another object of the present invention is to provide a sensor guide wire with a tip that is more resistant to permanent deformation and fatigue than prior art sensor guide wire tips.

According to one aspect the above mentioned objects are achieved by a sensor guide wire for intravascular measurements of at least one physiological or other variable in a living body, the sensor guide wire having a tip core wire portion comprising a shape memory material which is adapted such that the transformation temperature of the shape memory material is above body temperature of the living body.

Using a shape memory material in the core wire tip where the transformation temperature is above body temperature of the living body entails that when the sensor guide wire is used in a procedure within the living body, the shape memory material of the guide wire tip will be in its martensite form, i.e. the softer, shapeable form. If the user shapes the tip before insertion, the shape of the tip will enable easier steering of the tip through occasionally winding and tortuous vessels.

According to a further aspect the above mentioned objects are achieved by a sensor guide wire comprising a tip core wire portion where the distal tip comprises shape memory material which is adapted such that the transformation temperature of the shape memory material is above body temperature of the living body, and wherein a proximal portion of the tip comprises a superelastic material. In one embodiment, approximately the distal half of the tip comprises shape memory material, and approximately the proximal half of the tip core wire comprises superelastic or linear elastic material. In this embodiment, the advantages of using the superelastic or linear elastic properties when navigating through tortuous vessels and advantages of being able to reshape the tip due to the shape memory material are combined to produce a superior sensor guide wire tip.

The shape memory material in the present invention can be shape memory alloys or shape memory polymers. In a preferred embodiment, the shape memory material is nitinol.

The sensor guide wire according to aspects of the present invention provides a sensor guide wire in which the tip is easier to reshape by the user than in prior art sensor guide wires.

Furthermore, the sensor guide wire according to aspects of the present invention has improved navigation; facilitating maneuvering through the various bends and turns in the vessels.

In addition, the sensor guide wire according to aspects of the present invention comprises a tip that is more resistant to permanent deformation and fatigue than prior art sensor guide wire tips.

In another aspect, the sensor guide wire according to the present invention allows partial shaping and reshaping of the tip, according to the user's needs.

Throughout the specification, the word distal refers to the part located furthest away in respect of the operator, and the word proximal refers to the part located closest in respect of the operator.

Figure 1A:
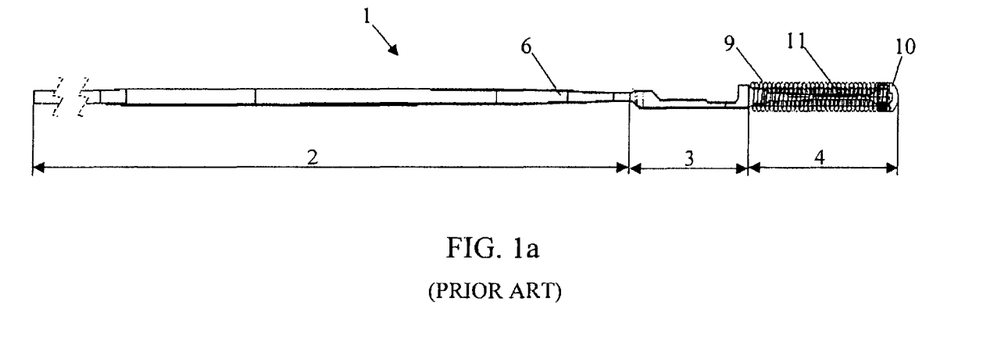
FIG. 1a illustrates schematically the general design of a sensor and guide wire assembly according to the prior art.
Figure 1B:
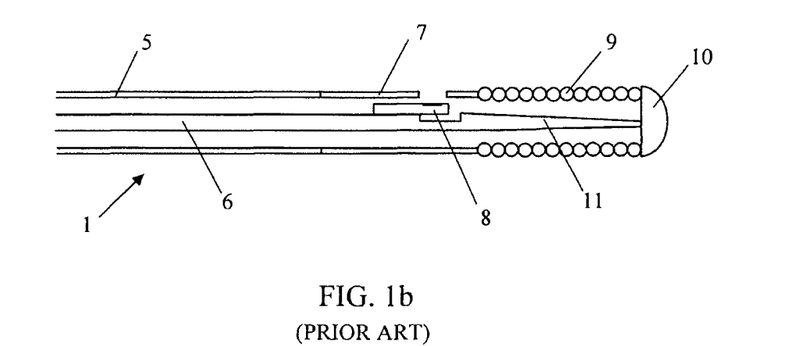
FIG. 1b further illustrates a sensor guide wire according to the prior art.

For better understanding of the context in which the present invention is going to be used, a sensor and guide wire assembly 1 of a conventional design is illustrated in FIGS. 1a and 1b. FIG. 1a illustrates a sensor guide wire 1 for intravascular measurements of at least one variable in a living body, wherein the sensor guide wire 1 has a proximal region 2, a distal sensor region 3 and a tip region 4. In FIG. 1b, a closer view of the distal sensor region 3 and tip region 4 is shown. The sensor guide wire 1 further comprises a hollow tube 5, a core wire 6, a jacket or sleeve 7, a sensor element or chip 8, a distal coil 9, a dome-shaped tip 10, and one or several electrical leads (not shown). The profile of the core wire 6 is shown schematically in FIG. 1b, for an example refer to FIG. 1a. For clarity, in FIG. 1a the hollow tube, jacket, and sensor element has been removed. A tip core wire portion 11 extends essentially along the tip region 4. The tip core wire portion 11 is schematically shown in FIG. 1b as having a tapering shape. However, tip core wire portions can have a variety of longitudinal and cross-sectional shapes. The distal coil 9 at least partly encloses the tip core wire portion 11. Preferably the distal coil 9 is radiopaque, such that it is visible using an X-ray imaging system.

Figure 2A:
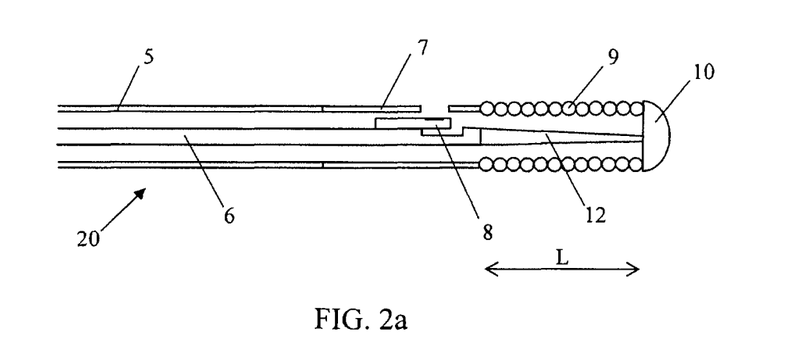
FIG. 2a shows a schematic longitudinal cross sectional view of a distal portion of a sensor guide wire according to one embodiment of the invention.
Figure 2B:
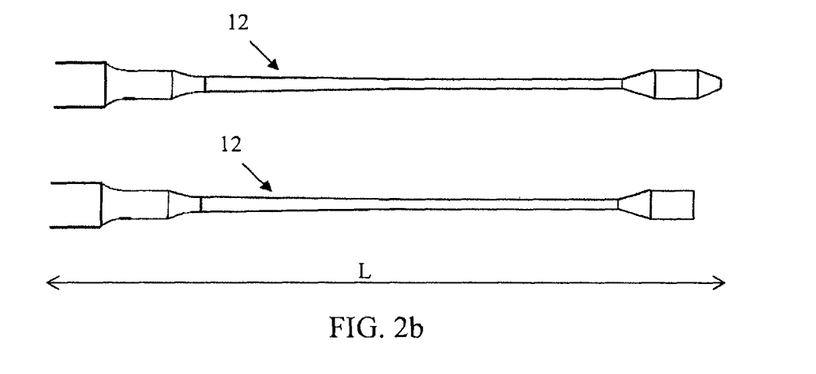
FIG. 2b shows two exemplary longitudinal profiles of a tip core wire portion of a sensor guide wire according to embodiments of the present invention.

In a first embodiment, shown in FIG. 2a, the present invention comprises a sensor guide wire 20 essentially according to the above description, wherein the sensor guide wire 20 comprises a hollow tube 5, a core wire 6, a jacket or sleeve 7, a sensor element or chip 8, a distal coil 9, a dome-shaped tip 10, and one or several electrical leads (not shown). However, in this embodiment the tip core wire portion 12 comprises a shape memory material in which the transformation temperature is above body temperature. Also in this embodiment, the entire core wire 6, including the tip core wire portion 12, can be formed in various longitudinal profiles and cross-sectional shapes, including the shape shown in FIG. 1a. Furthermore, examples of cross-sectional shapes of the tip core wire portion 12 includes, but is not limited to, round, elliptical, hexagonal, octagonal or square. Two preferred shapes of the tip core wire portion 12 are shown in FIG. 2b. In FIG. 2b, other elements of the sensor guide wire tip are eliminated for clarity; however it is understood that the core wire tip portion 12 is part of an assembly as illustrated in FIG. 2a. In these two embodiments the distal tip of the tip core wire portion 12 comprises a core wire with a circular cross-section in a plane perpendicular to the longitudinal axis. Such core wire tip shapes render the sensor guide wire flexible in all directions, and are described in e.g. WO 2012/041905, assigned to the present assignee, and incorporated herein by reference for medical devices, assemblies, and techniques described therein. The core wire tip portion 12 can comprise a varying diameter along the longitudinal axis of the wire. In the examples shown in FIG. 2b, the proximal end is wide, allowing attachment and/or support of a jacket housing a sensor. Distally of the jacket the wire can narrow down to add flexibility to the assembly. At the distal tip the diameter can increase to result in an enlarged distal core wire tip. In an embodiment of the present invention, a core wire tip portion 12 comprises shape memory material in which the transformation temperature is above body temperature, resulting in an improved sensor guide wire tip, as described below.

As mentioned above, using a shape memory material in the core wire tip where the transformation temperature is above body temperature of the living body entails that when the sensor guide wire is used in a procedure within the living body, the shape memory material of the guide wire tip will be in its martensite form, i.e. the softer, shapeable form. If the user shapes the tip before insertion, the shape of the tip will enable easier steering of the tip through occasionally winding and tortuous vessels. If removed from the living body, and subjected to a temperature above the transformation temperature, the tip will revert to the original shape. This will be described in detail below.

Notably, in some types of shape memory material, as has been described above, the transformation from one shape to another occurs gradually over a short range of degrees. However, as used herein, "transformation temperature" is herein defined as the temperature at which the shape memory material starts to recover to its original shape, i.e. starts to go through a phase change. For metal alloys, this is essentially equal to the austenite start temperature ($A_s$).

In a further embodiment, the present invention comprises a sensor guide wire comprising a shape memory material in which the composition is adapted such that the transformation temperature of the shape memory material is above 40 degrees Celsius, more preferably between 40 degrees Celsius and 70 degrees Celsius. Using this temperature range has the advantage of allowing the user to reshape the core wire tip by heating using any suitable technique, such as dipping in warm water or saline or heating by hot air. This will be further explained in detail in connection with the related method below.

The shape memory material of the tip core wire portion 12 can be any shape memory material in which it is possible to adapt the transformation temperature to above body temperature (37 degrees Celsius). Examples include shape memory polymers and shape memory metal alloys.

Examples of shape memory polymers that can be used in the present invention are: P(MMA-co-VP)PEG, copolyester, P(AA-co-MMA)-PEG, P(MA-co-MMA)-PEG corn oil polymer, PMMA-PBMA copolymers, epoxy, fish oil copolymers, PET-PEG copolymer, soybean oil copolymers with styrene and DVB, styrene copolymer, thermosetting polyurethanes, dehydrochlorinated cross-linked PVC, polynorbornene, high $M_W$ PMMA, poly-caprolactone, EVA and nitrile rubber, PE, poly-cyclooctene, PCO-CPE blend, PCL-BA copolymer, poly(ODVE)-co-BA, EVA and CSM. Advantages of using shape memory polymers, compared to some shape memory alloys, include having a high capacity for elastic deformation, much lower cost, lower density, easy processing, and potential biocompatibility and biodegradability.

Examples of shape memory alloys (and in some cases a preferred percentage of the respective metals) that can be used in the present invention are: Au—Cd (32-37 wt. % Cd), Ag—Cd (45-50 wt. % Cd), Cu—Al—Ni (14-14.5 wt. % Al and 3-4.5 wt. % Ni), Cu—Sn (approx. 25 wt. % Sn), Cu—Zn (38.5-41.5 wt. % Zn), Cu—Zn—X (X=Si, Al, Sn), Fe—Pt (approx. 54 wt. % Pt), Mn—Cu (5-37 wt. % Cu), Fe—Mn—Si, Pt alloys, Co—Ni—Al, Co—Ni—Ga, Ni—Fe—Ga, Ti—Pd, Ni—Ti (54-57 wt. % Ni), Ni—Ti—Nb, and Ni—Mn—Ga. The preferred ratios of the respective metals are approximate. As is well known in the art, the characteristics of a shape memory alloy and its transformation temperature are defined by several factors, such as ratio of individual metals, process parameters, additions of additives, etc.

In one preferred embodiment, the shape memory material is nitinol (Ni—Ti). Furthermore, the preferred composition of the nitinol is that which yields a transformation temperature, specifically an $A_s$ (austenite start temperature) of between 40 and 70 degrees Celsius, more preferably between 45 and 60 degrees Celsius.

For example, when using a shape memory nitinol with an $A_s$ of 55 degrees Celsius, the corresponding austenite finish temperature ($A_f$) will then be approximately 70-75 degrees Celsius, as the phase transformation from martensite to austenite occurs over a range of approximately 15-20 degrees. This ensures that, if a user heats the wire tip to above 75 degrees Celsius, full transformation to austenite occurs, and the wire tip reverts to its original shape, as will be described below.

In one embodiment, shown in FIGS. 2a and 2b, the entire tip core wire portion 12, from a short distance distal of the sensor element 8 to the distal tip of the core wire, is made of shape memory material. The tip core wire portion 12 has a length L, which is between 15 mm and 60 mm, preferably between 25 mm and 40 mm.

Figure 3:
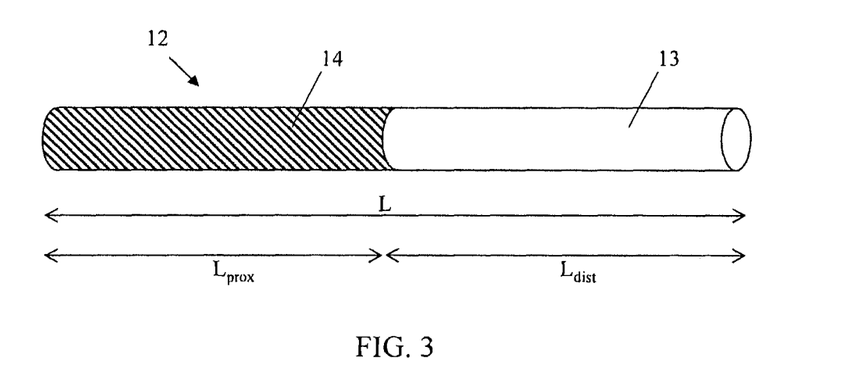
FIG. 3 shows a perspective view of a tip core wire portion of a sensor guide wire according to another embodiment of the invention.
Figure 4:
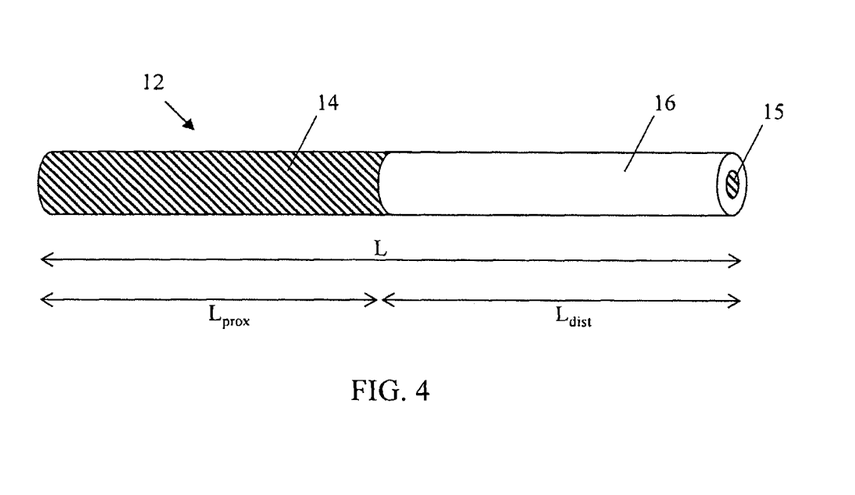
FIG. 4 shows a perspective view of a tip core wire portion of a sensor guide wire according to yet another embodiment of the invention.

Further embodiments are shown in FIGS. 3 and 4. For clarity, only the tip core wire portion 12 is shown in FIGS. 3 and 4. However, it is understood that the tip core wire portion 12 is provided within a configuration as that illustrated in FIG. 2a, i.e. within a distal coil 9, and adjacent to a sensor 8 mounted on a core wire 6. In addition, even though the distal tip is shown as a cylindrical form with a blunt end, other shapes of the tip core wire can be used, such as those illustrated in FIG. 2b. Furthermore, the shape can be cylindrical or a varying diameter profile with a rounded distal tip, an enlarged distal tip or a flattened shape.

In the embodiment illustrated in FIG. 3, at least a distal part 13 of the tip core wire portion 12 comprises shape memory material. The remaining proximal part 14 of the tip core wire portion 12 comprises an elastic material, preferably a non-shape memory material, such as stainless steel or a superelastic or linear elastic material, such as superelastic or linear elastic nitinol. This configuration will provide a tip with improved flexibility due to the elastic proximal part, combined with improved shapeability, due to the distal shape memory part. Compared to previously known sensor guide wires, this combination provides greatly improved maneuverability through e.g. tortuous blood vessels.

In the embodiment shown in FIG. 4, in the tip core wire portion 12, the center 15 of the proximal part 14 is extended distally to form a central core 15 within the distal part of the tip core wire portion 12, and the shape memory material is formed as a distal cover 16. The distal cover 16 is part of the core wire portion 12, and is therefore distinct from the jacket or sleeve 7 depicted in FIG. 2a. The center core 15, as an extension of the proximal part 14, thereby comprises an elastic material, preferably a non-shape memory material, such as stainless steel or a superelastic or linear elastic material, such as superelastic or linear elastic nitinol. Hereby, elastic features, due to the central core 15, are added to the distal tip, while maintaining the shape memory properties, due to the shape memory distal cover 16. This further improves maneuverability of the wire tip.

As in the previous embodiments, the tip core wire portion 12 of the embodiments illustrated in FIGS. 3 and 4 has a length L, which is between 15 mm and 60 mm, preferably between 25 mm and 40 mm. Furthermore, in the embodiment described in FIGS. 3 and 4, the distal part 13,16 of the tip core wire portion 12 has a length $L_{dist}$, and the proximal part 14 of the tip core wire portion has a length $L_{prox}$, wherein the sum of $L_{dist}$ and $L_{prox}$ is equal to the total length L of the tip core wire portion 12. In one embodiment $L_{dist}$ constitutes approximately 75% of the total length L. In another embodiment $L_{dist}$ constitutes approximately 50% of the total length L. In a preferred embodiment $L_{dist}$ constitutes approximately 25% of the total length L.

The shape, or outer profile, of the tip core wire portion 12 of the embodiments illustrated in FIGS. 3 and 4 is schematically shown as being cylindrical. However, as in previous embodiments, the tip core wire portion 12 can be formed in various longitudinal profiles and cross-sectional shapes, including the shapes shown in FIGS. 1*a*, 2*a* and 2*b*. Furthermore, examples of cross-sectional shapes of the tip core wire portion 12 include, but are not limited to, round, elliptical, hexagonal, octagonal or square. The two preferred shapes of the tip core wire portion 12 shown in FIG. 2*b* are applicable also when applying the embodiments of FIGS. 3 and 4, i.e. that the tip core wire portion comprises two parts, one distal region comprising shape memory material, and one proximal region comprising elastic material, such as linear elastic or superelastic nitinol, or stainless steel.

As discussed above, a sensor guide wire is advantageously provided with a core wire running along essentially the entire length of the sensor guide wire. This is also applied in the sensor guide wire according to embodiments of the present invention, with the difference that the distal part of the core wire, i.e. in the tip region 4, being the tip region core wire 12 as described herein.

In one embodiment the tip region core wire 12 is unitary with the remaining main core wire 6.

In another embodiment, the tip region core wire 12 is attached to the remaining core wire 6, by e.g. welding, soldering, gluing and other methods known in the art. In this embodiment the remaining core wire can be made of e.g. steel or nitinol. If nitinol is used, the composition of the nitinol in the remaining core wire can be the same as the nitinol in the tip region core wire, or another composition, thereby adapting the transformation temperature of the respective region.

In another embodiment the tip region core wire 12 is separate from the main core wire 6. In this embodiment the proximal part of the tip region core wire 12 is preferably attached to e.g. a jacket. This can be done by gluing, welding, soldering, mechanical attachment, swaging and other methods known in the art.

The sensor guide wire 1 may further comprise at least one microcable extending at least partly along the sensor guide wire 1 and being connected to the sensor element.

Using a tip core wire portion 12 made of shape memory material in which the transformation temperature is above body temperature of the living body in which it is to be used yields a sensor guide wire with a tip that is more flexible than conventional wires. If nitinol is used as the shape memory material, it will be in the martensite form when used within the body. This makes the sensor guide wire easier to navigate through tortuous blood vessels.

Furthermore, the distal tip according to the invention is less prone to deformation (e.g. kinking) and fatigue, which can lead to breaks, than conventional stainless steel tips.

Figure 5A:
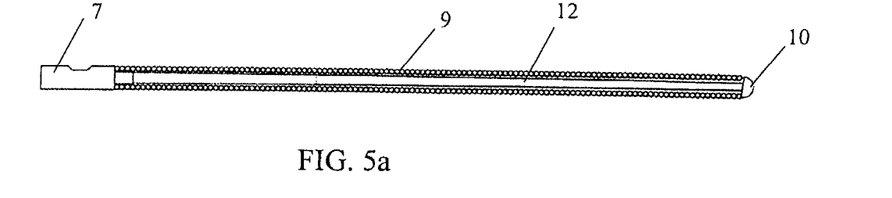
FIGS. 5a, 5b and 5c illustrate the shaping and reshaping of a core wire tip according to embodiments of the invention.
Figure 5B:
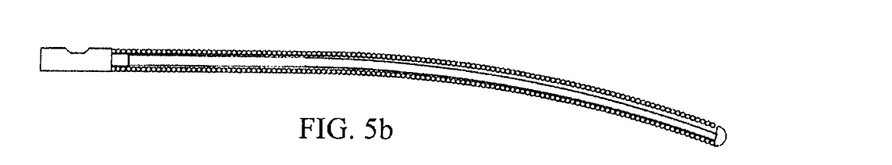
Figure 5C:
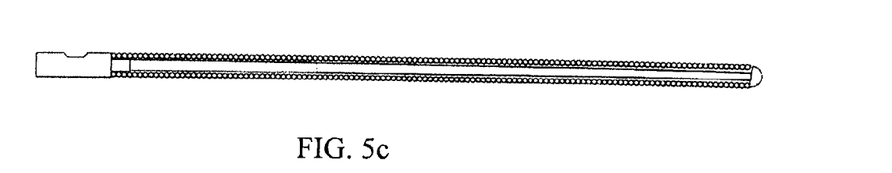

The sensor guide wire according to the present invention allows the user to easily shape and reshape the tip. When the sensor guide wire is delivered to the user it has a preformed shape, typically essentially straight, as illustrated in FIG. 5*a*. Depending on the procedure to be executed, the user can shape the tip to a desired shape. Before inserting the sensor guide wire into the body of a patient, for example into an opening into the femoral artery, the user shapes the tip manually by hand or with suitable tools. Commonly, the user will bend the tip at a slight angle, as illustrated in FIG. 5*b*. This is easily done, as the tip is flexible. Furthermore, the user is able to shape the tip at room temperature (approximately 18-24 degrees Celsius) without having to actively heat or cool the tip region. The ability to shape the tip at room temperature provides advantages over prior art guide wires that require heating and/or cooling steps to shape portions of the guide wire. For example, shaping at room temperature is easier and more efficient, which saves times during a medical procedure. After the user shapes the tip into the desired shape, the user inserts the wire into the body, typically via a short introducer into the blood stream. When performing procedures in the coronary arteries, a catheter has previously been placed such that the distal end is within the opening of a coronary artery, i.e. where the vessels start to narrow down and become more tortuous. The sensor guide wire is threaded through the catheter, and into the coronary arteries. Using the bended distal tip, the user can navigate through bends or turns by rotating and pushing the wire forward.

In these types of procedures, the user commonly wants to reshape the wire tip, for a change in navigational properties. As described in the background, this has traditionally been done by removing the wire from the patient's body, reshaping it manually by first straightening it, and thereafter re-bending at a new angle. This can be difficult with stainless steel tips, which are hard to fully straighten out, and are prone to fatigue breaks when bent and re-bent.

In the present invention, these problems are solved by using a tip core wire portion 12 comprising a shape memory material in which the transformation temperature is above body temperature of the living body in which the sensor guide wire is used. The present tip will allow the user to simply heat the tip to above the transformation temperature, causing the wire to instantly revert to the initial straight shape, without any kinks or remaining bends. In the embodiments using nitinol or other metal alloys as the shape memory material, heating to above the transformation temperature will cause the nitinol to change to the austenite form. The heating can be performed by any suitable technique, such as dipping in warm water or saline or heating by hot air. In the commonly sterile environment the sensor guide wire is used, sterile water or saline is preferred.

After reshaping the tip by heating, and removing the tip from the heat (and/or actively cooling the tip), it is easily bent into a new desired shape, due to the flexibility of the material. In the embodiments using nitinol or other metal alloys as the shape memory material, removing the tip from the heat and allowing it to cool, will revert the alloy back to the softer martensite form (and in some embodiments, the initial straight shape), in which the tip is easy to reshape.

The above example describes navigation through the coronary arteries. This is a non-limiting example, and the sensor guide wire according to the present invention can be used in a variety of procedures, where navigation through narrow and tortuous pathways is needed.

In another aspect, the tip region of the sensor guide wire comprising the tip core wire portion 12 can be partially reshaped by heat. For instance, the tip can only partially be inserted into a water or saline having a temperature of above the transformation temperature of the shape memory material, such as above 40 degrees Celsius, thereby only reverting part of the tip to the original shape.

In another embodiment, the sensor guide wire does not include a heater. In still another embodiment, the shape memory material of the tip core wire portion is not energized by an electrical current to cause a shape change. Rather, the shape change of the shape memory material is caused by application of an external heat source (such as heated water, saline, or air).

Figure 6:
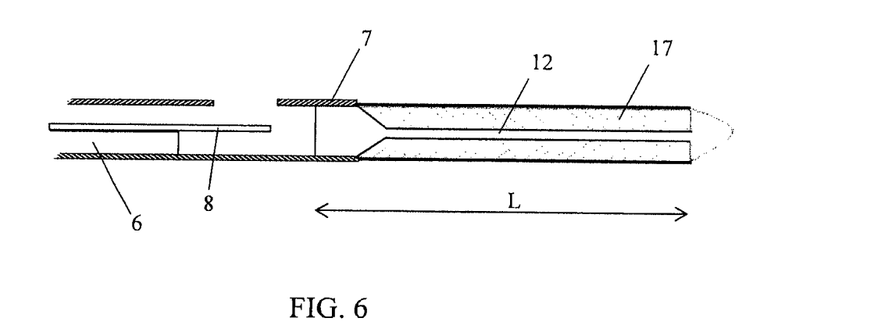
FIG. 6 shows a distal portion of a sensor guide wire according to a further embodiment.

In yet another embodiment, the sensor guide wire is essentially as described in the above embodiments, wherein the tip core wire portion 12 comprises a shape memory material and the distal coil is replaced with a flexible polymer layer 17. This is illustrated in FIG. 6. Preferably, the polymer layer 17 is radiopaque to make the wire tip visible by X-rays on an angiogram. In FIG. 6, the tip core wire portion 12 is shown as being separate from the main core wire 6 and attached to a jacket 7, but as described above, the tip core wire portion 12 can also be unitary with or attached to the main core wire 6. Furthermore, tip core wire portion 12 can comprise a shape memory distal tip and a superelastic or linear elastic proximal part, as described above.

The present invention is not limited to the above-described preferred embodiments. Various alternatives, modifications and equivalents may be used. Therefore, the above embodiments should not be taken as limiting the scope of the invention, which is defined by reference to the appended claims.

What is claimed is:

1. A sensor guide wire for intravascular measurement of at least one physiological or other variable in a living body, comprising:
    a proximal region, a distal sensor region located distal of the proximal region, and a tip region located distal of the distal sensor region;
    at least one sensor element arranged in the sensor region, and comprising a sensor portion, configured to measure the variable and generate a sensor signal in response to the variable;
    a core wire comprising a proximal core wire portion extending at least partially along the proximal region of the sensor guide wire, and a tip core wire portion extending at least partially along the tip region of the sensor guide wire;
    wherein the proximal core wire portion is made of a non-shape memory material or a shape memory material having a transformation temperature below 37° C., and
    wherein at least part of said tip core wire portion comprises a shape memory material having a transformation temperature in a range of 40° C. to 70° C.

2. The sensor guide wire according to claim 1, wherein at least 25% of a length of the tip core wire portion comprises the shape memory material having a transformation temperature in a range of 40° C. to 70° C.

3. The sensor guide wire according to claim 1, wherein at least 50% of a length of the tip core wire portion comprises the shape memory material having a transformation temperature in a range of 40° C. to 70° C.

4. The sensor guide wire according to claim 1, wherein a remaining portion of the tip core wire portion comprises a non-shape memory material or a shape memory material having a transformation temperature below 37° C.

5. The sensor guide wire according to claim 4, wherein the shape memory material having a transformation temperature in a range of 40° C. to 70° C. is arranged distally to the portion of the tip core wire portion that comprises the non-shape memory material or the shape memory material having a transformation temperature below 37° C.

6. The sensor guide wire according to claim 4, wherein said shape memory material having a transformation temperature in a range of 40° C. to 70° C. is arranged as an outer layer on at least a distal part of said portion of the tip core wire portion that comprises the non-shape memory material or the shape memory material having a transformation temperature below 37° C.

7. The sensor guide wire according to claim 4, wherein the material of the remaining portion of the tip core wire portion is stainless steel.

8. The sensor guide wire according to claim 4, wherein the material of the remaining portion of the tip core wire portion is superelastic or linear elastic nitinol.

9. The sensor guide wire according to claim 1, wherein the shape memory material having a transformation temperature in a range of 40° C. to 70° C. is nitinol.

10. The sensor guide wire according to claim 1, wherein the shape memory material having a transformation temperature in a range of 40° C. to 70° C. is a shape memory polymer.

11. The sensor guide wire according to claim 1, wherein the tip core wire portion is unitary with the proximal core wire portion.

12. The sensor guide wire according to claim 1, wherein the tip core wire portion is separate from the proximal core wire portion and is attached to a jacket by at least one of gluing, welding, soldering, mechanical attachment, or swaging.

13. The sensor guide wire according to claim 1, wherein the tip core wire portion is attached to a remaining core wire by at least one of gluing, welding, soldering, mechanical attachment, or swaging.

14. The sensor guide wire according to claim 1, wherein the proximal core wire portion is made of stainless steel.

15. The sensor guide wire according to claim 1, wherein the proximal core wire portion is made of superelastic nitinol or linear elastic nitinol.

* * * * *